United States Patent [19]

Taniuchi et al.

[11] Patent Number: 4,783,563

[45] Date of Patent: Nov. 8, 1988

[54] PREPARATION OF HEXABROMOCYCLODODECANE

[75] Inventors: Akira Taniuchi, Kyoto; Takuji Nakano, Kusatsu; Setsuo Nishibori, Otsu, all of Japan

[73] Assignee: Dai-Ichi Kogyo Seiyaku Co., Ltd., Kyoto, Japan

[21] Appl. No.: 149,339

[22] Filed: Jan. 28, 1988

[30] Foreign Application Priority Data

Jan. 29, 1987 [JP] Japan .................................. 62-019288

[51] Int. Cl.⁴ ............................................... C07C 17/02
[52] U.S. Cl. ...................................... 570/246; 570/186
[58] Field of Search .................................. 570/246, 186

[56] References Cited

U.S. PATENT DOCUMENTS 3,558,727  1/1971  Jenkner et al. ....................... 570/246

Primary Examiner—Howard T. Mars
Attorney, Agent, or Firm—Millen & White

[57] ABSTRACT

Hexabromocyclododecane may be synthesized at a high yield in pure form by brominating 1,5,9-cyclododecatriene with bromine in a $C_4$–$C_8$ saturated aliphatic alcohol in the presence of a boron trifluoride complex, neutralizing the reaction mixture with a non-aqueous base, and recovering the resulting crystals of hexabromocyclododecane.

6 Claims, No Drawings

PREPARATION OF HEXABROMOCYCLODODECANE

BACKGROUND OF THE INVENTION

This invention reaates to a method for preparing hexabromocyclododecane.

Hexabromocyclododecane has been widely used as a flame retardant for molded or foamed thermoplastic products such as those made of polyolefin or polystyrene. It also finds use in the fireproofing treatment of textile products in the form of a latex or water-suspension.

Hexabromocyclododecane may be synthesized by brominating 1,5,9-cyclododecatriene. It is desirable for the resulting product to be colorless and free of low melting point by-products as far as possible, particularly when it is intended to use with high impact strength polystyrene resins comprising polyolefin, polystyrene and styrene-butadiene copolymer.

In the conventional process, the bromination of 1,5,9-cyclododecatriene is carried out in a solvent such as ethanol. The mother liquor from which crystals of the resulting hexabromocyclododecane are separated is reused in the next bromination reaction.

This known process, however, suffers from certain disadvantages in that the product is contaminated with significant amounts of low melting point by-products. Further purification requires washing the raw product with a large amount of solvent such as clean ethanol one or several times. This, of course, increases cost while decreasing the yield of pure product.

SUMMARY OF THE INVENTION

It is therefore an object of the present invention to provide an improved method for producing hexabromocyclododecane which gives the product in purer form at higher yields.

This and other objects are accomplished by providing a method for preparing hexabromocyclododecane which comprises the steps of reacting 1,5,9-cyclododecatriene with bromine in a $C_4$-$C_8$ saturated aliphatic alcohol in the presence of a catalytically effective amount of a boron trifluoride complex, neutralizing the reaction mixture with a non-aqueous base, and recovering the resulting crystals of hexabromocyclododecane.

DETAILED DISCUSSION

The method of the present invention is characterized by the use of a $C_4$-$C_8$ saturated aliphatic alcohol as a reaction solvent as well as the use of a boron trifluoride complex as a catalyst in the bromination of 1,5,9-cyclododecatriene.

Alcohols usable for this purpose preferably have a solubility parameter (S.P.) of about 9.2 to about 11.5. They may be straight or branched chain alkanols or a cycloalkanol having 4-8 carbon atoms. Examples thereof include n-butyl alcohol (S.P. 10.7), isobutyl alcohol (S.P. 10.8), n-amyl alcohol (S.P. 10.6), isoamyl alcohol (S.P. 10.0), n-hexyl alcohol (S.P. 10.0), cyclohexanol (S.P. 11.4) and n-octyl alcohol (S.P. 10.3). Mixtures of these alcohols such as fusel oil (S.P. 10.3) may also be used.

Examples of boron trifluoride complexes include boron trifluoride-ethyl ether complex, boron trifluoride-phenol complex, boron trifluoride-amine complexes, boron trifluoridemethanol complex and boron trifluoride-acetic acid complex.

The amount of the above reaction solvent is not critical provided that the exothermic reaction may be conveniently controlled. The amount of boron trifluoride complex catalyst is generally from 0.5 to 2%, preferably about 1% by weight of the solvent.

The amount of bromine ranges between 3.0 and 3.2 moles as $Br_2$ per mole of 1,5,9-cyclododecatriene. This amount of bromine may be added dropwise to the mixture of 1,5,9-cyclododecatriene and the solvent containing the catalyst. Alternatively, bromine may be added concurrently with 1,5,9-cyclododecatriene to the reaction solvent containing the catalyst.

The reaction temperature may be below 40° C., preferably below 30° C.

After the completion of the bromination reaction, the reaction mixture is neutralized to a pH about 8.0 to 8.5 with an amount of non-aqueous base such as a solution of sodium methoxide, sodium ethoxide, potassium butoxide, sodium isobutoxide or sodium isoamyloxide in the corresponding alcohol, triethylamine, triethanolamine, diethanolamine, monoethanolamine, butylamine, ethylamine, cyclohexylamine, trimethylamine, pyridine or alcoholic solutions of these amines or ammonia.

After the neutralization, crystals of hexabromocyclododecane are filtered off and washed thoroughly with hot water or hot lower alkanol or both. The crystals may be washed further with dilute aquous ammonia if necessary. After drying, hexabromocyclododecane may be obtained at a high yield in a pure state.

The following examples illustrate the invention. All parts and percents therein are by weight unless otherwise indicated.

EXAMPLE 1

A flask was charged with 420 g of isobutyl alcohol containing 4.2 g of boron trifluoride-ethyl ether complex. Then 495 g (3.09 mols) of bromine and 162 g (1 mol) of 1,5,9-cyclododecatriene were concurrently added dropwise to the flask while maintaining the temperature at 20°–30° C. After the addition, the reaction mixture was stirred for 2 hours and then cooled to 20° C. The mixture was neutralized to pH8.0–8.5 with a 20% solution of sodium methoxide in methanol. The resulting crystals were filtered off, washed with 320 g of boiling methanol and then 1% aqueous ammonia, successively, and dried at 50° C. 559 g (87% of theory) of hexabromocyclododecane was obtained. Properties of the product are shown in Table 1.

EXAMPLES 2–3 AND COMPARATIVE EXAMPLES 1–2

The procedure of Example 1 was repeated except that the solvent and catalyst were substituted with other solvents and catalysts listed in Table 1. The results are also shown in Table 1.

TABLE 1

| Example | Solvent, g | Catalyst, g | Neutralizing Agent | Yield, g (% theory) | M.P. °C. | Heu[1] | Heat Resistance[2] |
|---|---|---|---|---|---|---|---|
| 1 | Isobutyl alcohol | $BF_3$/ethyl ether | 20% $CH_3ONa$ in $CH_3OH$ | 559 (87) | 179 | 10 | Good |

TABLE 1-continued

| Example | Solvent, g | Catalyst, g | Neutralizing Agent | Yield, g (% theory) | M.P. °C. | Heu[1] | Heat Resistance[2] |
|---|---|---|---|---|---|---|---|
| 2 | Isoamyl alcohol 420 | BF$_3$/butyl ether 4.2 | 20% CH$_3$ONa in CH$_3$OH | 545.7 (85) | 182 | 10 | Good |
| 3 | Isobutyl alcohol 420 | BF$_3$/acetic acid 4.2 | 20% CH$_3$ONa in CH$_3$OH | 473.9 (74) | 193 | 10 | Good |
| Comparative Ex. 1 | n-Butanol 420 | — | 20% CH$_3$ONa in CH$_3$OH | 436.6 (68) | 176 | 60 | Not good |
| Comparative Ex. 2 | Ethanol 420 | BF$_3$/ethyl ether 4.2 | 20% CH$_3$ONa in CH$_3$OH | 430.2 (67) | 168 | 120 | Not good |

[1] APHA of 2% acetone solution.
[2] 2.5 g of sample is heated at 120° C. for 5 hours in a 100 ml beaker. Judgement is made visually based on the entire color and the number of black spots.

EXAMPLES 4–6 AND COMPARATIVE EXAMPLES 3–4

Using various solvents and catalysts listed, in Table 2, the procedure of Example 1 was repeated. However, the whole amount of cyclododecatriene was charged initially and only the bromine was added dropwise. The results are shown in Table 2.

TABLE 2

| Example | Solvent, g | Catalyst, g | Neutralizing Agent | Yield, g (% theory) | M.P. °C. | Heu | Heat Resistance |
|---|---|---|---|---|---|---|---|
| 4 | Fusel oil 420 | BF$_3$/ethyl ether 4.2 | Diethanolamine | 532.9 (83) | 179 | 30 | Good |
| 5 | Isobutyl alcohol 420 | BF$_3$/methanol 4.2 | Monoethanolamine | 526.5 (82) | 180 | 20 | Good |
| 6 | Isobutyl alcohol 420 | BF$_3$/butyl ether 4.2 | 15% Na isobutoxide in isobutyl alcohol | 494.4 (77) | 181 | 20 | Good |
| Comparative Ex. 3 | Isopropyl alcohol 420 | BF$_3$/butyl ether 4.2 | 28% NH$_4$OH | 385.2 (60) | 136 | 140 | Not good |
| Comparative Ex. 4 | n-propyl alcohol 420 | — | Ethylenediamine | 430.2 (67) | 167 | 90 | Not good |

EXAMPLES 7–8 AND COMPARATIVE EXAMPLES 5–6

Using various solvents, catalysts and neutralizing agents listed in Table 3, the procedure of Example 1 was repeated. However, crystals recovered from the neutralized mixture were washed with 400 g of boiling water containing a small amount of aqueous ammonia and dried at 50°–80° C.

The results are shown in Table 3.

APPLICATION EXAMPLE 100 parts of polystyrene resin, 3.5 parts of hexabromocyclododecane obtained in the above Example 1, 2 or 4 or comparative Example 1 or 4, 0.03 parts of di-n-octyl maleate polymer and 0.03 parts of dioctylphenyl phoshite were kneaded on a hot roll mill at 180°–190° C. for 6 minutes. The resulting compound was pressed into a sheet at 180°–190° C. at 200 atms for 3 minutes and cooled.

Each specimen was tested for color change, flame retardancy (oxygen index) and viscosity change. The results are shown in Table 4.

TABLE 3

| Example | Solvent, g | Catalyst, g | Neutralizing Agent | Yield, g (% theory) | M.P. °C. | Heu | Heat Resistance |
|---|---|---|---|---|---|---|---|
| 7 | Isobutyl alcohol 420 | BF$_3$/ethyl ether 4.2 | 20% CH$_3$ONa in CH$_3$OH | 565 (88) | 178 | 35 | Good |
| 8 | Isoamyl alcohol 420 | BF$_3$/ethyl ether 4.2 | 20% Isoamyl ONa in isoamyl OH | 552.2 (86) | 180 | 30 | Good |
| Comparative Ex. 5 | n-Buthyl alcohol 420 | — | 20% Isoamyl ONa in isoamyl OH | 436.6 (68) | 171 | 60 | Not good |
| Comparative Ex. 6 | Ethyl alcohol 420 | — | 20% Isoamyl ONa in isoamyl OH | 430.2 (67) | 160 | 200 | Not good |

TABLE 4

| | Hexabromocyclododecane | | | | |
|---|---|---|---|---|---|
| | Ex. 1 | Ex. 2 | Ex. 4 | Comp. Ex. 1 | Comp. Ex. 4 |
| Color change[1] | No change | No change | No change | Slightly changed | Totally changed |
| Oxygen index[2] | 28.1 | 28.1 | 28.1 | 27.2 | 26.4 |
| Decrease in viscosity, %[3] | 96.4 | 95.8 | 94.0 | 89.2 | 79.4 |

[1]Visually judged compared with a standard specimen containing no flame retardant.
[2]O. I. test according to ASTM D-2863-70.
[3]% retention of the viscosity of the starting polystyrene resin. Measurement is made at 25° C. at a concentration of 0.5 g/100 ml toluene using Cannon-Fenske viscometer.

We claim:

1. A method for preparing hexabromocyclododecane which comprises the steps of reacting 1,5,9-cyclododecatriene with bromine in a $C_4$–$C_8$ saturated aliphatic alcohol in the presence of a catalytically effective amount of a boron trifluoride complex, neutralizing the reaction mixture with a non-aqueous base, and recovering the resulting crystals of hexabromocyclododecane.

2. The method according to claim 1, wherein said alcohol has a solubility parameter of 9.2 to 11.5.

3. The method according to claim 1, wherein said alcohol is n- or iso-butyl alcohol, n- or isoamyl alcohol, n-hexyl alcohol, n-octyl alcohol, cyclohexanol or a mixture thereof.

4. The method according to claim 1, wherein said boron trifluoride complex is a complex with a lower alkyl ether, an amine, phenol, methanol or acetic acid.

5. The method according to claim 1, wherein said non-aqueous base is a solution of alkali metal lower alkoxide in the corresponding alcohol, an amine or a solution of said amine or ammonia in a lower alkanol.

6. The method according to claim 1 further including the step of washing said crystals with hot water or hot lower alkanol.

* * * * *